United States Patent
Lee et al.

(10) Patent No.: US 12,164,014 B2
(45) Date of Patent: Dec. 10, 2024

(54) SYSTEMS AND METHODS OF MEASURING AND CORRECTING EFFECTS OF CONCOMITANT FIELDS IN A MAGNETIC RESONANCE SYSTEM

(71) Applicant: GE PRECISION HEALTHCARE LLC, Wauwatosa, WI (US)

(72) Inventors: Seung-Kyun Lee, Cohoes, NY (US); Afis Ajala, Schenectady, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 184 days.

(21) Appl. No.: 18/156,127

(22) Filed: Jan. 18, 2023

(65) Prior Publication Data

US 2024/0241204 A1 Jul. 18, 2024

(51) Int. Cl.
*G01R 33/565* (2006.01)
*A61B 5/055* (2006.01)

(52) U.S. Cl.
CPC ........ *G01R 33/56518* (2013.01); *A61B 5/055* (2013.01); *G01R 33/56536* (2013.01)

(58) Field of Classification Search
CPC .............. A61B 5/055; G01R 33/56518; G01R 33/56536
See application file for complete search history.

(56) References Cited

U.S. PATENT DOCUMENTS 10,613,174 B2  4/2020  Bhat
10,712,420 B2  7/2020  Shengzhen et al.
11,243,287 B2  2/2022  Harris
(Continued)

FOREIGN PATENT DOCUMENTS

EP   3304098 A1   4/2018
WO   2016180983 A1  11/2016
WO   2016196103 A1  12/2016

OTHER PUBLICATIONS

Abad et al.,. "Brain Microstructure Imaging with Ultrahigh B-Encoding using MAGNUS High Performance Gradients", in ISMRM 2022 Annual Proceedings (2022).
(Continued)

*Primary Examiner* — Gregory H Curran
(74) *Attorney, Agent, or Firm* — Armstrong Teasdale LLP

(57) ABSTRACT

A method for measuring concomitant fields in a magnetic resonance (MR) system is provided. The method includes applying a measurement pulse sequence in a plurality of acquisitions. Applying the measurement pulse sequence further includes applying a first bipolar gradient pulse in a first acquisition, applying a second bipolar gradient pulse in reverse polarities from the first bipolar gradient pulse in a second acquisition, and applying the measurement pulse sequence without a bipolar gradient pulse in a third acquisition. The method further includes acquiring MR signals emitted from the subject, and generating phase images based on the MR signals. The method also includes generating volumetric vector field maps based on the phase images, wherein the volumetric vector field maps include concomitant field at each spatial location in a 3D volume, the concomitant field represented as a vector. In addition, the method includes outputting the volumetric vector field maps.

20 Claims, 13 Drawing Sheets
(1 of 13 Drawing Sheet(s) Filed in Color)

(56) References Cited

U.S. PATENT DOCUMENTS

| | | | |
|---|---|---|---|
| 11,294,016 | B1 | 4/2022 | Foo |
| 11,474,184 | B2 * | 10/2022 | Ferguson ............ G01R 33/5617 |
| 11,686,798 | B2 * | 6/2023 | Roberts .............. G01R 33/5608 |
| | | | 324/309 |
| 2009/0309596 | A1 | 12/2009 | Feiweier |
| 2013/0057281 | A1 | 3/2013 | Feiweier |
| 2018/0203088 | A1 | 7/2018 | Tao et al. |
| 2021/0103022 | A1 | 4/2021 | Harris et al. |
| 2021/0149003 | A1 | 5/2021 | Wang et al. |
| 2021/0166447 | A1 | 6/2021 | Koerzdoerfer |
| 2023/0095599 | A1 | 3/2023 | Roberts |

OTHER PUBLICATIONS

Abad et al., Calibration of concomitant field offsets using phase-contrast MRI for asymmetric gradient coils, Magn Reson Med. Jan. 2023;89(1):262-275. doi: 10.1002/mrm.29452. Epub Sep. 21, 2022.

Ajala et al., "3D Pseudo-Continuous Arterial Spin Labeling Acquisition using a High-Performance Gradient System: A Scan Time and Image Quality Assessment", in ISMRM 2022 Annual Proceedings (2022).

Bernstein et al., "Concomitant Gradient Terms in Phase Contrast MR: Analysis and Correction", MRM 39:300-308 (1998).

Du et al., "Correction of Concomitant Magnetic Field-Induced Image Artifacts in Nonaxial Echo-Planar Imaging" MRM 48:509-515 (2002), DOI: 10.1002/mrm.10249.

Foo et al., "Highly efficient head-only magnetic field insert gradient coil for achieving simultaneous high gradient amplitude and slew rate at 3.0T (MAGNUS) for brain microstructure imaging", Magnetic Resonance in Medicine 83, 2356-2369 (2019).

King et al, "Concomitant Gradient Field Effects in Spiral Scans", MRM 41:103-112 (1999).

Setsompop et al., "Pushing the limits of in vivo diffusion MRI for the Human Connectome Project", Neuroimage 80, 220-233 (2013).

Shih et al.,. "Initial Clinical Experience with MAGNUS Ultra-High-Performance Gradient Coil for Diffusion Microstructure Imaging of Intracranial Pathology", in ISMRM 2022 Annual Proceedings (2022).

Tao et al.,. "The Effect of Concomitant Fields in Fast Spin Echo Acquisition on Asymmetric MRI Gradient Systems" Magn Reson Med 79, 1354-1364 (2018).

Tao et al., "Gradient Pre-Emphasis to Counteract First-Order Concomitant Fields on Asymmetric MRI Gradient Systems", MRM 77:2250-2262 (2017), published online Jul. 4, 2016, DOI: 10.1002/mrmt.26315.

Weavers et al., "B0 Concomitant Field Compensation for MRI Systems Employing Asymmetric Transverse Gradient Coils", MRM 79:1538-1544 (2018), published online Jun. 21, 2017, DOI: 10.1002/mrm.26790.

Weiger et al.,. "A high-performance gradient insert for rapid and short-T2 imaging at full duty cycle", Magn Reson Med 79, 3256-3266 (2018).

Wilm et al., Single-Shot Spiral Imaging Enabled by an Expanded Encoding Model: Demonstration in Diffusion MRI, MRM, 77:83-91, published onine Oct. 21, 2016, DOI: 10.1002/mrm.26493.

Yudilevich et al., "Interpolation from Samples on a Linear Spiral Scan", IEEE Trans Med Imaging, 1987;6(3):193-200, doi: 10.1109/TMI.1987.4307827.

Zhou et al., "Artifacts Induced by Concomitant Magnetic Field in Fast Spin-Echo Imaging", MRM 40:582-591 (1998).

Zhu et al., "Characterizing Restricted Diffusion in Pre-/Post-treatment Gliomas Using Time-dependent Diffusion MRI at Ultra-high-gradient Human 3.0T", in ISMRM 2022 Annual Proceedings (2022).

Niu C. et al., "A Novel Active Shim Coil Design Scheme for the Effective Imaging Region above the Patient Bed in MRI", J Supercond Nov Magn 35, 1685-1691 (2022). https://doi.org/10.1007/s10948-022-06249-x.

Christoph Juchem et al., "Dynamic multi-coil shimming of the human brain at 7T", Journal of Magnetic Resonance, vol. 212, Issue 2, 2011, pp. 280-288, ISSN 1090-7807, https://doi.org/10.1016/j.jmr.2011.07.005.

Liao et al., "Flexible use of AC/DC shim array for eddy-currents and concomitant fields mitigation with demonstrated applications in diffusion-prepared acquisition and non-Cartesian sampling", in ISMRM 2023 Workshop on Data Sampling & Image Reconstruction, published Jan. 3, 2023.

* cited by examiner

SYSTEMS AND METHODS OF MEASURING AND CORRECTING EFFECTS OF CONCOMITANT FIELDS IN A MAGNETIC RESONANCE SYSTEM

BACKGROUND OF THE INVENTION

The field of the disclosure relates generally to systems and methods of medical imaging, and more particularly, to systems and methods of measuring and correcting effects of concomitant fields in a magnetic resonance (MR) system.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

Concomitant fields generated by gradients in an MR system introduce errors in the MR signals and therefore may interfere with diagnosis. Known methods are disadvantaged in some aspects and improvements are desired.

SUMMARY OF THE INVENTION

In one aspect, a method for measuring concomitant fields in a magnetic resonance (MR) system is provided. The method includes applying a measurement pulse sequence in a plurality of acquisitions with a subject positioned in an MR system. Applying the measurement pulse sequence further includes applying a first bipolar gradient pulse in a first acquisition, applying a second bipolar gradient pulse in reverse polarities from the first bipolar gradient pulse in a second acquisition, and applying the measurement pulse sequence without a bipolar gradient pulse in a third acquisition. The method further includes acquiring MR signals emitted from the subject, and generating phase images based on the MR signals. The method also includes generating volumetric vector field maps based on the phase images, wherein the volumetric vector field maps include concomitant field at each spatial location in a three-dimensional (3D) volume, the concomitant field represented as a vector. In addition, the method includes outputting the volumetric vector field maps.

In another aspect, a method for measuring concomitant fields in an MR system is provided. The method includes applying a measurement pulse sequence in a plurality of acquisitions with a subject positioned in an MR system, wherein applying a measurement pulse sequence further includes varying the measurement pulse sequence in the plurality of acquisitions. The method also includes acquiring MR signals emitted from the subject, generating phase images based on the MR signals, and isolating concomitant fields from other perturbation fields of the MR system based on the phase images. The method further includes generating volumetric vector field maps based on the phase images, wherein the volumetric vector field maps include concomitant field at each spatial location in a 3D volume, and the concomitant field is represented as a vector. Further, the method includes outputting the volumetric vector field maps.

In one more aspect, a method for measuring concomitant fields in an MR system is provided. The method includes measuring transverse concomitant fields by applying a measurement pulse sequence in a plurality of acquisitions, applying a measurement pulse sequence further including varying the measurement pulse sequence in the plurality of acquisitions. The method also includes measuring a z field by applying the measurement pulse sequence including a z field measurement pulse sequence.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

The disclosure includes systems and methods of measuring and correcting effects of concomitant fields in a magnetic resonance (MR) system. Concomitant fields introduce errors to MR signals and cause artifacts such as pixel shifts, in-plane blurring, and/or through-plane blurring in MR images of a subject. As used herein, a subject is a human, an animal, or a phantom, or part of a human, an animal, or a phantom, such as an organ or tissue. An MR system is described herein as an example for illustration purposes only. Systems and methods described herein may be applied to other image modalities such as PET-MR (positron emission tomography-magnetic resonance) systems. Method aspects will be in part apparent and in part explicitly discussed in the following description.

In magnetic resonance imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as $B_0$ and extends in the longitudinal or z direction. In acquiring an MRI image, a magnetic field (referred to as an excitation field $B_1$), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal $B_1$ is terminated. To use the MR signals to generate an image of a subject, magnetic field gradient pulses ($G_x$, $G_y$, and $G_z$) are used. The gradient pulses are used to scan through the k-space, the space of spatial frequencies or inverse of distances. A Fourier relationship exists between the acquired MR signals and an image of the subject, and therefore the image of the subject may be derived by Fourier transform of the MR signals.

Figure 1:
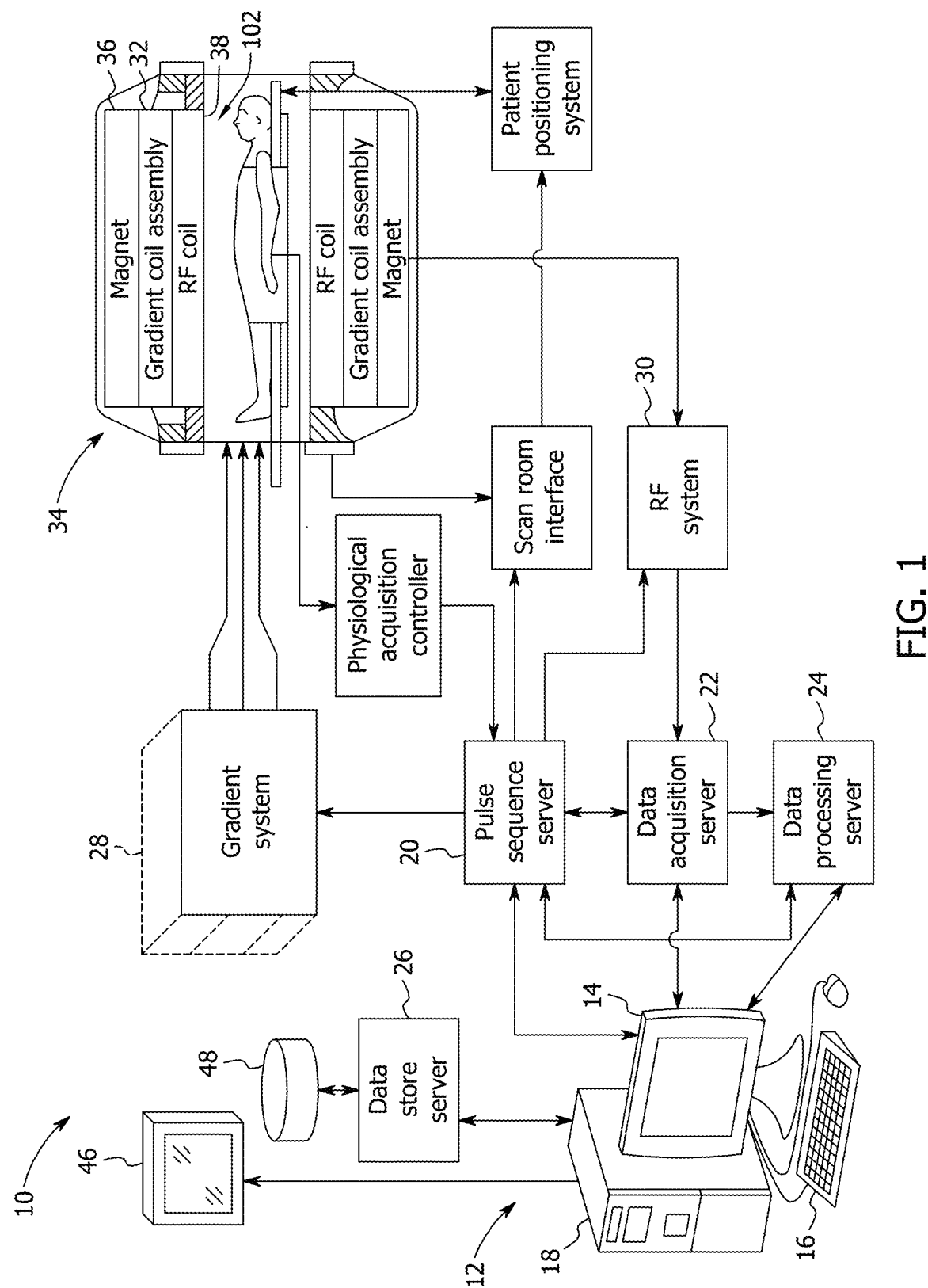
FIG. 1 is a schematic diagram of an example magnetic resonance (MR) system.

FIG. 1 illustrates a schematic diagram of an example MR system 10. In the example embodiment, MR system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MR system 10. Workstation 12 is coupled to a pulse sequence server 20, a data acquisition server 22, a data processing server 24, and a data store server 26. Workstation 12 and each server 20, 22, 24, and 26 communicate with each other.

In the example embodiment, pulse sequence server 20 responds to instructions downloaded from workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. RF coil 38 is shown as a whole body RF coil. RF coil 38 may also be a local coil that may be placed in proximity to the anatomy to be imaged, or a coil array that includes a plurality of coils.

In the example embodiment, gradient waveforms used to perform the prescribed scan are produced and applied to gradient system 28, which excites gradient coils in gradient coil assembly 32 to produce the magnetic field gradients $G_x$, $G_y$, and $G_z$ used for position-encoding MR signals. Gradient coil assembly 32 forms part of a magnet assembly 34 that also includes a polarizing magnet 36 configured to generate a polarizing magnetic field $B_0$ and RF coil 38.

In the example embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil 38 by RF system 30. Responsive MR signals detected by RF coil 38 are received by RF system 30, amplified, demodulated, filtered, and digitized under direction of commands produced by pulse sequence server 20. RF coil 38 is described as a transmit and receive coil such that RF coil 38 transmits RF pulses and detects MR signals. In one embodiment, MR system 10 may include a transmit RF coil that transmits RF pulses and a separate receive coil that detects MR signals. A transmission channel of RF system 30 may be connected to a RF transmission coil and a receiver channel may be connected to a separate RF receive coil. Often, the transmission channel is connected to the whole body RF coil 38 and each receiver section is connected to a separate local RF coil.

In the example embodiment, RF system 30 also includes one or more RF receiver channels. Each RF receiver channel includes an RF amplifier that amplifies the MR signal received by RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2}; \quad (1)$$

and the phase of the received MR signal may also be determined as in Eq. (2) below:

$$\varphi = \tan^{-1}\left(\frac{Q}{I}\right). \quad (2)$$

In the example embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20. Also, navigator signals may be acquired during a scan and used to adjust the operating parameters of RF system 30 or gradient system 28, or to control the view order in which k-space is sampled.

In the example embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the example embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. Workstation 12 may be used by an operator to archive the images, produce films, or send the images via a network to other facilities.

In MR, when the amplitude of gradients are increased, effects of concomitant fields increase. Concomitant fields result from the principle that under Maxwell's equations, there cannot be magnetic monopoles ($\nabla \cdot \vec{B}=0$) or rotation in the field ($\nabla \times \vec{B}=0$) in current source-free space. Concomitant fields cause time and spatial varying phase variance for each sample point ($k_x$, $k_y$, $k_z$) in the k-space. Such unwanted phase may cause artifacts and errors such as image shift in EPI, blurring in spiral imaging, signal loss in fast spin echo, and inaccuracies in phase-contrast velocity mapping. Correction of concomitant field offset is particularly needed for high-performance gradient coils and in compact head-only scanners, where the amplitudes of the gradients are increased.

Effects of lower orders of concomitant fields such as the spatially uniform and linear components of concomitant fields may be corrected by gradient pre-emphasis or RF modulation. High-order concomitant terms, however, are not corrected by gradient pre-emphasis and/or RF modulation. The significance of effects of high-order concomitant terms in images increases drastically as the gradient amplitude increases and as field strength decreases because the high order concomitant field terms are a function of the square of the gradient strength and is inversely proportional with the field strength. As used herein, the order in a high-order concomitant field term refers to spatial variation of the concomitant field term, and an order is the order of the function of the concomitant field with respect to the spatial location x, y, or z. For example, if a concomitant field term is a function of $x^2$, the concomitant field term is a second-order concomitant field term.

A direct solution to reduce errors from concomitant fields is to increase the field strength of magnet 36. This solution is infeasible because upgrading the field strength of an MR system, such as from 1.5 T to 3 T, would essentially be replacing the entire MR system and would be too expensive.

To reduce the effects of the concomitant fields in an MR system, a user may have to resort to not using the maximum gradient strength provided by the gradient coil assembly in a pulse sequence, failing to take a full advantage of capability of the gradient hardware. On the other hand, high-performance gradient coils with increased maximum gradients have increased importance in clinical applications. Accordingly, there is a long-felt need in correcting concomitant fields, especially high order concomitant fields, with increased accuracy.

In some known methods, high-order concomitant terms are approximated by estimating parameters for approximate mathematical expressions. The approximation, however, is based on the assumption of a linear gradient field, which assumes that an imaging gradient produces an incremental magnetic field whose intensity varies linearly with distance from the magnet isocenter. Gradient linearity, however, falls off significantly the father one gets from the isocenter for real gradient coils. Ignoring nonlinearity in gradients results in errors in characterization and correction of concomitant fields. For example, the error may be greater than 100 Hz at 5 G/cm for a 3.0 T head-only/narrow-bore gradient coil, resulting in uncorrected artifacts. Errors from using gradient linearity as an approximation increase for gradient coils having relatively high maximum amplitude and/or systems having a relatively low field strength. In another known method, a dynamic field camera is used to capture concomitant fields. The captured concomitant fields are specific to a pulse sequence. Calibration needs to be performed for each pulse sequence, rendering the method cumbersome and time consuming. Further, the number of probes installed in the system is limited, restricting the spatial coverage of this approach. In addition, the added hardware is expensive and also adds additional costs in installation and maintenance. In one more known method, concomitant fields are derived based on the gradient coil electromagnetic (EM) design. Gradient coil EM design is not always available. Further, this known approach does not account for manufacturing and assembling tolerances and/or errors.

In contrast, the systems and methods describe herein measure volumetric vector field maps for a gradient coil without the assumption of linearity, thereby increasing the accuracy in characterization and correction of effects from concomitant fields. The volumetric vector field maps include field vectors at each spatial location at any given time during scanning or sampling through the k-space, providing an actual k-space trajectory with an increased accuracy. The measurement is performed one time for a gradient coil and the measured volumetric vector maps may be used for any imaging pulse sequence. Gradient coil EM design or additional hardware is not needed. Further, measurement of concomitant fields with increased accuracy enables determination of field components for monitoring peripheral nerve stimulation and eddy current heating. Measurement of concomitant fields with increased accuracy also enables verifying whether a gradient coil EM design has met the design specification.

Figure 2:
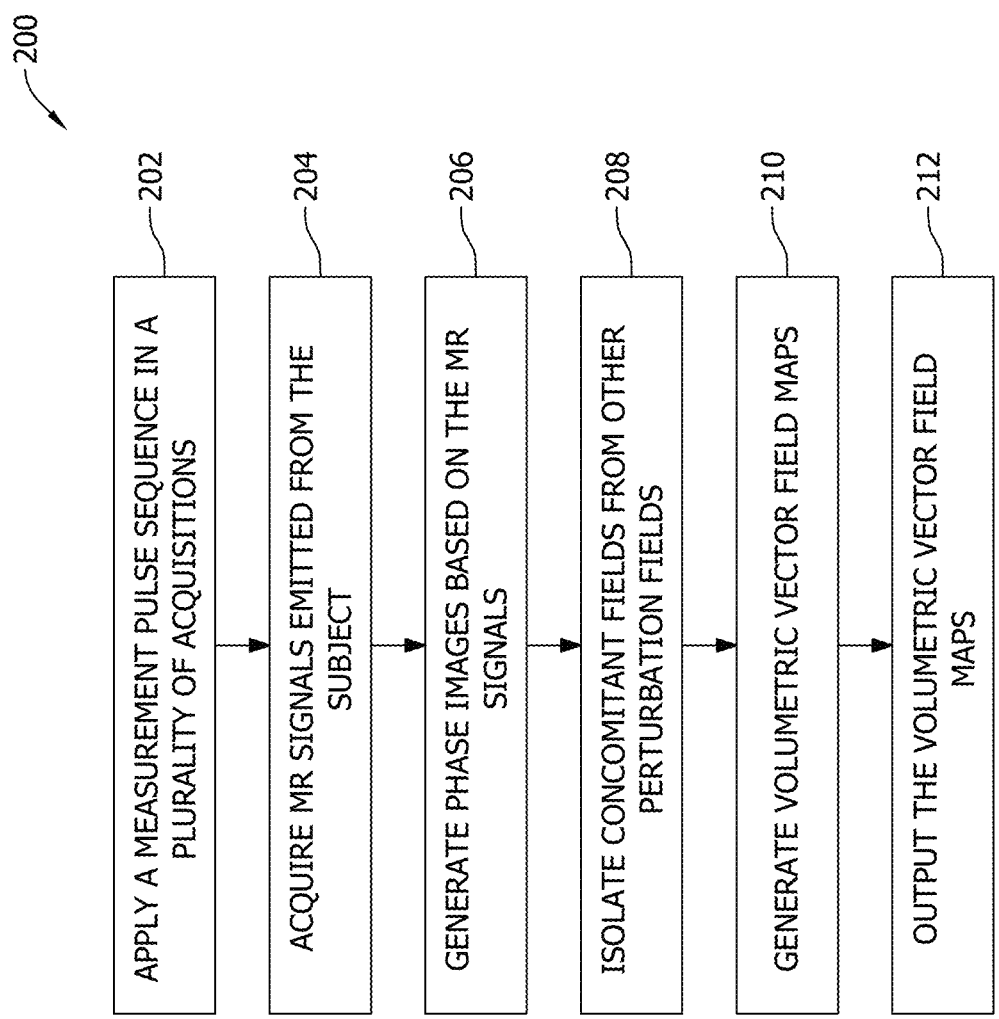
FIG. 2 is a flow chart of an example method of measuring concomitant fields.

FIG. 2 is a flow chart of an example method 200 of measuring concomitant fields. In the example embodiment, method 200 includes applying 202 a measurement pulse sequence in a plurality of acquisitions with a subject positioned in an MR system. The subject may be a phantom. In MR, a pulse sequence or a sequence is a sequence of RF pulses, gradient pulses, and data acquisition applied by MR system 10 in acquiring MR signals. The measurement pulse sequence is varied from one acquisition to another acquisition. Method 200 further includes acquiring 204 MR signals emitted from the subject. Method 200 also includes generating 206 phase images based on the MR signals. In MR, complex MR images may be reconstructed based on I and Q quadrature MR signals (see Eqn. (2)), using processes such as Fourier transform. Complex MR images $\rho(x, y)$ are MR images with each pixel represented by a complex number, which has a real component $Re(\hat{\rho}(x, y))$ and an imaginary component $Im(\hat{\rho}(x, y))$, with $(x, y)$ being the location of the pixel in an image. Magnitude of a complex MR image, referred to as a magnitude image, is generated as $|\hat{\rho}(x, y)| = \sqrt{Re(\hat{\rho}(x,y))^2 + Im(\hat{\rho}(x,y))^2}$. A phase image, phase of a complex MR image, is generated with phases $$\Phi(x, y) = \tan^{-1}\left(\frac{Im(\hat{\rho}(x, y))}{Re(\hat{\rho}(x, y))}\right)$$

(see Eqn. (2)).

In the example embodiment, method 200 further includes isolating 208 concomitant fields from other perturbation fields based on the phase images. In MR, perturbation fields are deviations of the magnetic field from the main magnetic field such as 1.5 T or 3.0 T. Causes of perturbation fields may be field inhomogeneity, eddy currents from the application of varying magnetic fields, and concomitant fields from gradient fields.

Figure 3:
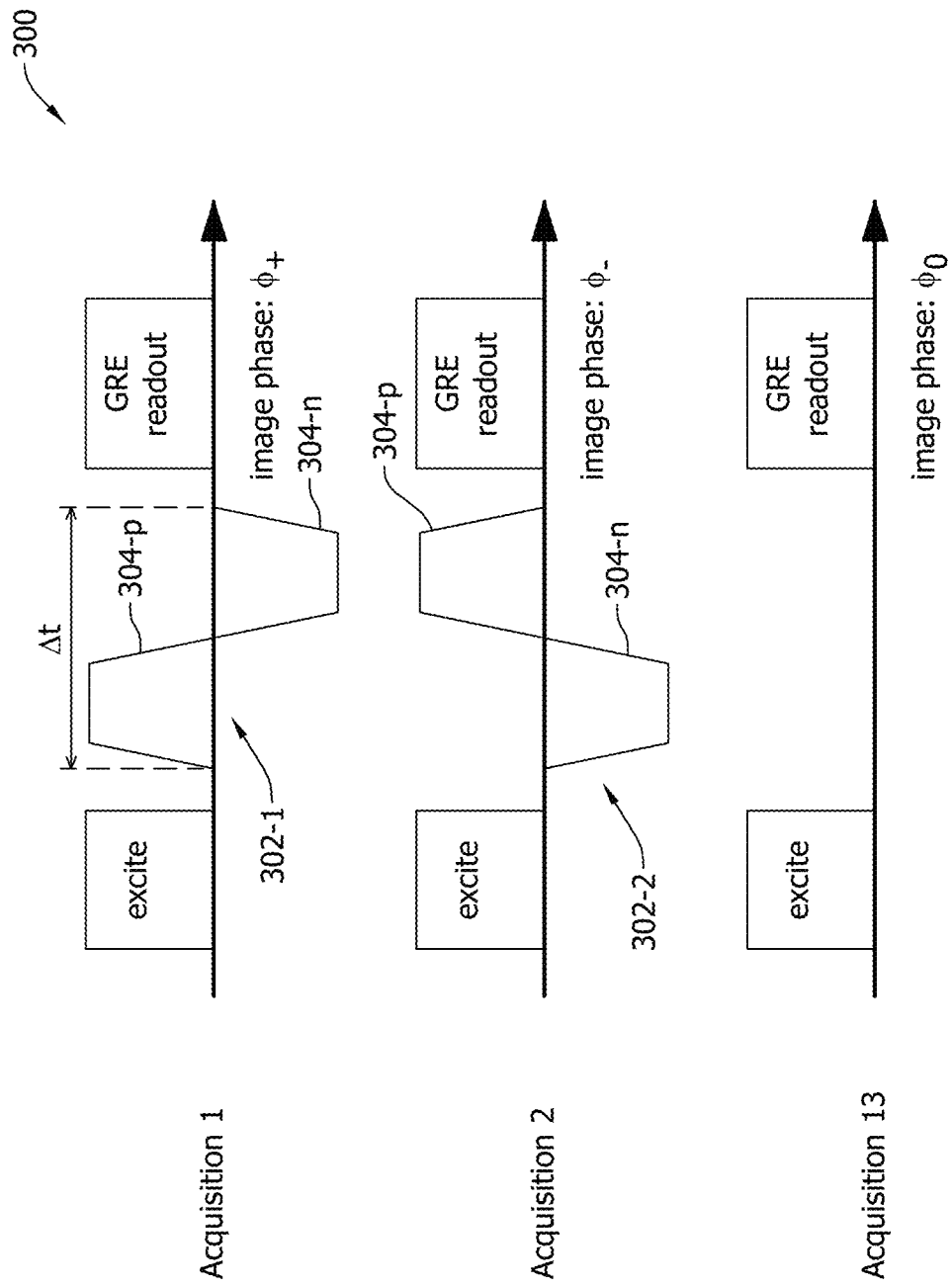
FIG. 3 is a schematic diagram of a measurement pulse sequence used in the method shown in FIG. 2.

FIG. 3 is a schematic diagram of a measurement pulse sequence 300 for measuring concomitant fields. In the example embodiment, three acquisitions are used. Measurement pulse sequence 300 includes a measurement gradient pulse 302 used to measure concomitant fields. A bipolar gradient pulse is an example measurement gradient pulse. A bipolar gradient pulse includes two consecutive gradient pulses with opposite polarities from one another. Bipolar gradient pulse 302 includes a positive lobe 304-$p$ and a negative lobe 304-$n$. The total area of bipolar gradient pulse 302 is zero, where positive lobe 304-$p$ and negative lobe 304-$n$ have the same areas under the pulse but opposite polarities. In Acquisitions 1 and 2, bipolar gradient pulses 302 are applied. First bipolar gradient pulse 302-1 in acquisition 1 and second bipolar gradient pulse 302-2 have reverse polarities from one another, where first bipolar gradient pulse 302-1 starts with a positive lobe 304-p followed with a negative lobe 304-n while second bipolar gradient pulse 302-2 starts with a negative lobe 304-n followed with a positive lobe 304-p. In Acquisition 3, bipolar gradient pulse 302 is not applied. Phase images ($\phi_+$ for Acquisition 1, $\phi_-$ for Acquisition 2, and $\phi_0$ for Acquisition 3) of images acquired in Acquisitions 1-3 are generated based on the acquired MR signals (see Eqn. (2)). The phase images are used to determine transverse concomitant field.

The total magnetic field $\vec{B}_{tot}$ of magnet assembly 34 at a location in a bore 102 of magnet assembly 34 (see FIG. 1) when a gradient field $B_g$ is applied may be expressed as below.

$$\vec{B}_{tot} = B_T \hat{x} + (B_0 + B_s + B_g + B_e)\hat{z} = B_T \hat{x} + (B_0 + B_z)\hat{z}, \quad (3)$$

where $B_T$ is concomitant field, $B_0$ is the main magnetic field such as 1.5 T or 3.0 T, $B_s$ is the static field inhomogeneity such as shim imperfection, $B_e$ is the magnetic field generated by eddy currents induced from changing magnetic fields in an MR system either from gradients or RF coils, $B_z$ is used to denote all field perturbation of MR system to the main magnetic field $B_0$ in the z direction, $\hat{x}$ denotes the unit vector in the transverse direction, which may be any unit vector in the x-y plane but x is used for simplicity, and $\hat{z}$ is the unit vector in the z direction. Transverse eddy current fields are ignored because in actively shielded gradient coils, the eddy current fields are on the order of 1% of the applied gradient fields at the edge of the field view whereas $B_T$ is on the same order of magnitude as the applied gradient fields. The distinction in including fields in $\hat{x}$ or $\hat{z}$ is not due to the fields' magnitudes, but due to the fields' directions, where whether the fields are in the transverse or longitudinal directions matters. If the field is transverse, the end effect of the field is much reduced compared to a longitudinal field of the same magnitude. Therefore, only transverse fields that are relatively strong need to be included in Eq. (3).

When $B_0\hat{z}$ is perturbed with $B_z\hat{z}$ in the longitudinal direction and with $B_T\hat{x}$ in the transverse direction, the individual effects from the longitudinal and transverse perturbation may be added to determine the total effects on the magnetic field. Let $\delta$ denote the relative amplitude of perturbation, where $$\delta = \max\left(\frac{B_z}{B_0}, \frac{B_T}{B_0}\right),$$

the total magnetic field may be expressed as:

$$B_{tot} = B_0\left(1 + \frac{B_z}{B_0} + \frac{1}{2} \cdot \frac{B_T^2}{B_0^2}\right) + O(\delta^3). \quad (4)$$

The instantaneous Larmor frequency in the rotating frame may be approximated as:

$$f(t) = \left(\frac{\gamma}{2\pi}\right)(B_{tot} - B_0) = \frac{\gamma}{2\pi} \cdot \left(B_s + B_g(t) + B_e(t) + \frac{1}{2} \cdot \frac{B_T^2(t)}{B_0}\right), \quad (5)$$

and the phase accumulated due to a first bipolar gradient pulse 302 with zero zeroth moment or area is as follows:

$$\phi_+ = 2\pi \int_0^{\Delta t} f(t)dt = \gamma\left(B_s\Delta t + 0 + \int_0^{\Delta t} B_e(t)dt + \frac{1}{2B_0} \cdot \int_0^{\Delta t} B_T^2(t)dt\right), \quad (6)$$

where $\Delta t$ is the duration of the bipolar gradient pulse (see FIG. 3). A zeroth moment or area is the integration of the area under the pulse. For example, G(t) is a function of t, and the zeroth moment of G(t) over a time period $\Delta t$ is $\int_0^{\Delta t} G(t)dt$.

When the measurement is repeated with a second bipolar gradient pulse 302-2, which has reverse polarities from the first bipolar gradient pulse 302-1, the accumulated phase is the same as that in Eqn. (6), except for the part from eddy current field being in a negative sign, and is expressed as:

$$\phi_- = \gamma\left(B_s\Delta t + 0 - \int_0^{\Delta t} B_e(t)dt + \frac{1}{2B_0} \cdot \int_0^{\Delta t} B_T^2(t)dt\right). \quad (7)$$

The phase in the same time period without the gradient pulse is as follows:

$$\phi_0 = \gamma B_s \Delta t. \quad (8)$$

The combination of the three phases in Eqn. (6)-(8) yields:

$$\phi_c \equiv \frac{\phi_+ + \phi_-}{2} - \phi_0 = \frac{\gamma}{2B_0} \cdot \int_0^{\Delta t} B_T^2(t)dt. \quad (9)$$

Accordingly, the concomitant field $B_T$ is isolated from other perturbation terms and may be measured from phase images. The phase combination also cancels any image phase that is not dependent on the bipolar gradient pulses, such as an RF phase, and eddy current fields that originate from other pulses in the pulse sequence. Isolating concomitant field $B_T$ from other perturbation terms by combining phases is based on the following insights. First, the transverse eddy current field is negligible compared to the transverse gradient field. Second, the z-direction eddy current field is linear to the current and changes the sign when the current waveform changes the sign. Third, the total phase due to the nominal, or z-direction, gradient field is zero for a bipolar pulse. Fourth, the square of the transverse gradient field is an even function of current. Fifth, it is a relatively good approximation to reality that transverse perturbation field is decoupled from z-directional perturbation field.

Referring back to FIG. 2, in the example embodiment, method 200 further includes generating 210 volumetric vector field maps based on the phase images. The combination phase image $\phi_c$ includes only phases accumulated from concomitant fields, and may be referred to as concomitant phase image $\phi_c$. Volumetric vector field maps may be generated based on the combination phase image $\phi_c$. The volumetric vector field maps include concomitant field at each spatial location in a three-dimensional (3D) volume, with the full gradient magnetic field including concomitant field represented as a vector. The vector has three components ($B_x$, $B_y$, $B_z$) in the x, y, or z direction, respectively. Each gradient coil $G_x$, $G_y$, $G_z$ has a corresponding volumetric vector field map. $G_x$ and $G_y$ gradient coils may be referred to as transverse gradient coils. $G_z$ gradient coil may be referred to as a longitudinal gradient coil. The volumetric vector field maps are normalized by the current produced by the corresponding gradient coil in the measurement pulse sequence. Method 200 also includes outputting 212 the volumetric vector field maps.

The transverse concomitant field per unit current (b, in the unit of T/A) produced by a gradient coil may be derived as follows, where volumetric vector field maps are normalized. Br is proportional to the current applied to the gradient coil as:

$$B_T(t) \equiv b \cdot I(t). \tag{10}$$

The concomitant phase is:

$$\phi_c = kb^2, \tag{11}$$

where $$k \equiv \frac{\gamma}{2B_0} \cdot I_{rms}^2 \cdot \Delta t \tag{12}$$

is a constant that is determined by the current waveform of the gradient pulses. Accordingly, the map of transverse magnetic field of a given gradient coil per unit current may be obtained by:

$$b(x, y, z) = \sqrt{\frac{\phi_c(x, y, z)}{k}}. \tag{13}$$

The concomitant field $B_T$ determined by phase combination as described above does not distinguish between the transverse field components (x and y), and is the total transverse field, where $$B_T = \sqrt{B_x^2 + B_y^2}. \tag{14}$$

The individual transverse components $B_x$ and $B_y$ produced by an x gradient ($G_x$) coil may be expressed as the below equations.

$$B_x = -\cos^2\varphi \cdot \frac{\partial \psi}{\partial \rho} - \sin^2\varphi \cdot \frac{\psi}{\rho}, \tag{15}$$

$$B_y = -\sin\varphi\cos\varphi \cdot \left(\frac{\partial \psi}{\partial \rho} - \frac{\psi}{\rho}\right), \tag{16}$$

where ($\rho$, $\varphi$) are polar coordinates of a transverse position (x, y) in an axial slice with $\rho$ as the radial distance of the transverse position from the z axis and $\varphi$ as the azimuthal angle of the transverse position relative to the x-axis, and $\psi$ is the ($\rho$, z)-dependent part of the magnetic scalar potential $\Phi$, which, for $G_x$, has the form $\Phi = \psi(\rho, z) \cos \varphi$. In a coordinate system for an MR system, the origin is at the isocenter of the MR system, the z axis is along the longitudinal direction of the magnetic field, and the x and y axis is along a transverse plane orthogonal to the z axis. In Eqns. (15) and (16), at coronal ($\varphi$=0) and $$\text{sagittal}\left(\varphi = \frac{\pi}{2}\right)$$

midplanes, $B_y$=0 and $B_x$ is given by:

$$B_x(\varphi = 0) = -\frac{\partial \psi}{\partial \rho}(\text{coronal midplane}), \tag{17}$$

$$B_x\left(\varphi = \frac{\pi}{2}\right) = -\frac{\psi}{\rho}(\text{sagittal midplane}). \tag{18}$$

A midplane is a plane crossing the isocenter of MR system 10. A coronal midplane is a coronal plane crossing the z axis. A sagittal midplane is a sagittal plane crossing the z axis. On the coronal and sagittal midplanes, because $B_y$=0, the transverse field measured by phase combination is equal to $B_x$. Based on Eqn. (17) and (18), the measured $B_x$'s at the two midplanes may be used to replace the two scalar potential expressions $$\frac{\partial \psi}{\partial \rho}$$

and $$\frac{\psi}{\rho}.$$

As a result, individual components $B_x$ and $B_y$ of the transverse field at any azimuthal angle may be derived based on Eqns. (15) and (16), thereby generating a 3D map of the concomitant field for the $G_x$ gradient coil.

Similarly, the transverse field vector of a $G_y$ gradient coil is obtained by measuring transverse field on the coronal and sagittal midplanes as:

$$B_x = -\cos\varphi\sin\varphi \cdot \left(\frac{\partial \psi}{\partial \rho} - \frac{\psi}{\rho}\right), \tag{19}$$

$$B_y = -\sin^2\varphi \cdot \frac{\partial \psi}{\partial \rho} - \cos^2\varphi \cdot \frac{\psi}{\rho}. \tag{20}$$

On the coronal and sagittal midplanes $B_x$=0, and $B_y$ is given as:

$$B_y(\varphi = 0) = -\frac{\psi}{\rho}(\text{coronal midplane}), \tag{21}$$

$$B_y\left(\varphi = \frac{\pi}{2}\right) = -\frac{\partial \psi}{\partial \rho}(\text{sagittal midplane}). \tag{22}$$

Accordingly, a volumetric vector field map for the $G_y$ gradient coil is generated with the field maps of the coronal and sagittal midplanes, where individual components $B_x$ and $B_y$ of the transverse field at any azimuthal angle may be derived based on Eqn. (19) and (20) using the field maps for the coronal and sagittal midplanes (Eqns. (21) and (22)).

For $G_z$ gradient coil, because $G_z$ gradient is axi-symmetric, where field at each position in z along an axial plane is the same, the magnetic field vector does not have an azimuthal component and does not depend on or vary with the azimuthal angle. The only transverse component, orthogonal to z, is the radial component (the ρ component). Measuring the radial component using phase images with bipolar gradient pulses as the measurement gradient pulses on any plane that contains the z axis such as the coronal or sagittal midplane, is sufficient to determine $B_ρ$ and therefore the full vector magnetic field of the z gradient coil.

The volumetric vector field maps may be used to correct effects of concomitant fields (see FIG. 7 described later). Correction field maps of an imaging pulse sequence may be derived by multiplying the volumetric vector field maps of a gradient coil with currents produced by the gradient coil in the imaging pulse sequence. The correction field maps are spatiotemporal functions, where the concomitant fields vary as functions of time and spatial locations. The correction field maps may be used to correct effects of concomitant fields in MR images.

In some embodiments, volumetric vector field maps may be used to determine concomitant fields that are significant in peripheral nerve stimulation and/or eddy current heating in the bore, increasing the accuracy in monitoring the safety of the subject in an MR system. In other embodiments, volumetric vector field maps may be used to verify EM design of a magnet assembly 34 to ensure that the components of the gradients are realized as designed. Such a verification is not presently available in known methods.

Figure 4:
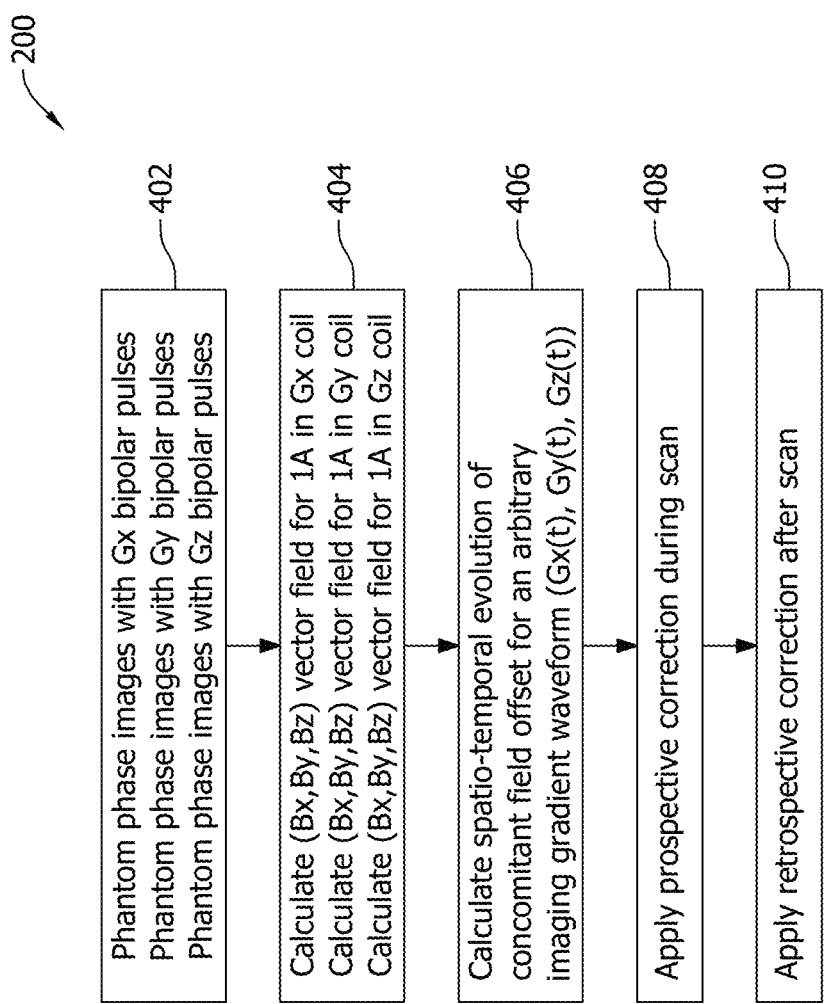
FIG. 4 is a flow chart of an example embodiment of the method shown in FIG. 2.

FIG. 4 is an example embodiment of method 200. In the example embodiment, phantom phase images with $G_x$ bipolar pulses or bipolar pulses applied along a $G_x$ direction, phantom phase images with $G_y$ bipolar pulses, phantom phase images with $G_z$ bipolar pulses are acquired 402. Vector fields ($B_x$, $B_y$, $B_z$) for unit current are calculated 404 for $G_x$, $G_y$, and $G_z$ coils. Spatial-temporal evolution of concomitant field for an arbitrary imaging gradient waveform ($G_x(t)$, $G_y(t)$, $G_z(t)$) is calculated 406. As used herein, the calculated concomitant field for the imaging gradient is referred to as correction field maps. Prospective correction may be applied 408 during scan using the correction field maps, for example using a concomitant field correction coil or pulse sequences configured to correct concomitant fields. Alternatively, correction field maps may be used in retrospective correction 410, which is applied after scan by correcting effects from concomitant fields on the acquired MR signals using the correction field maps. In some embodiments, prospective and retrospective corrections are applied, where retrospective correction is used to correct residual errors from effects of the concomitant fields that remain uncorrected after the prospective correction.

In operation, for an MR system, volumetric vector field maps are measured using a measurement pulse sequence 300 for each gradient coil, where the volumetric vector field maps are normalized to unit current. The measurement only needs to be performed once for an MR system to generate volumetric vector maps for the $G_x$, $G_y$, or $G_z$ gradient coil. The measurement may be periodically performed to update with system changes. The actual concomitant fields corresponding to each pulse sequence, or correction field maps, are generated based on the volumetric vector field maps, for example by multiplying the volumetric vector field maps with the current applied to the gradient coil in the pulse sequence. The correction field maps may be used to retrospectively and/or prospectively correct the effects from concomitant fields on the images acquired with the pulse sequence.

Figure 5A:
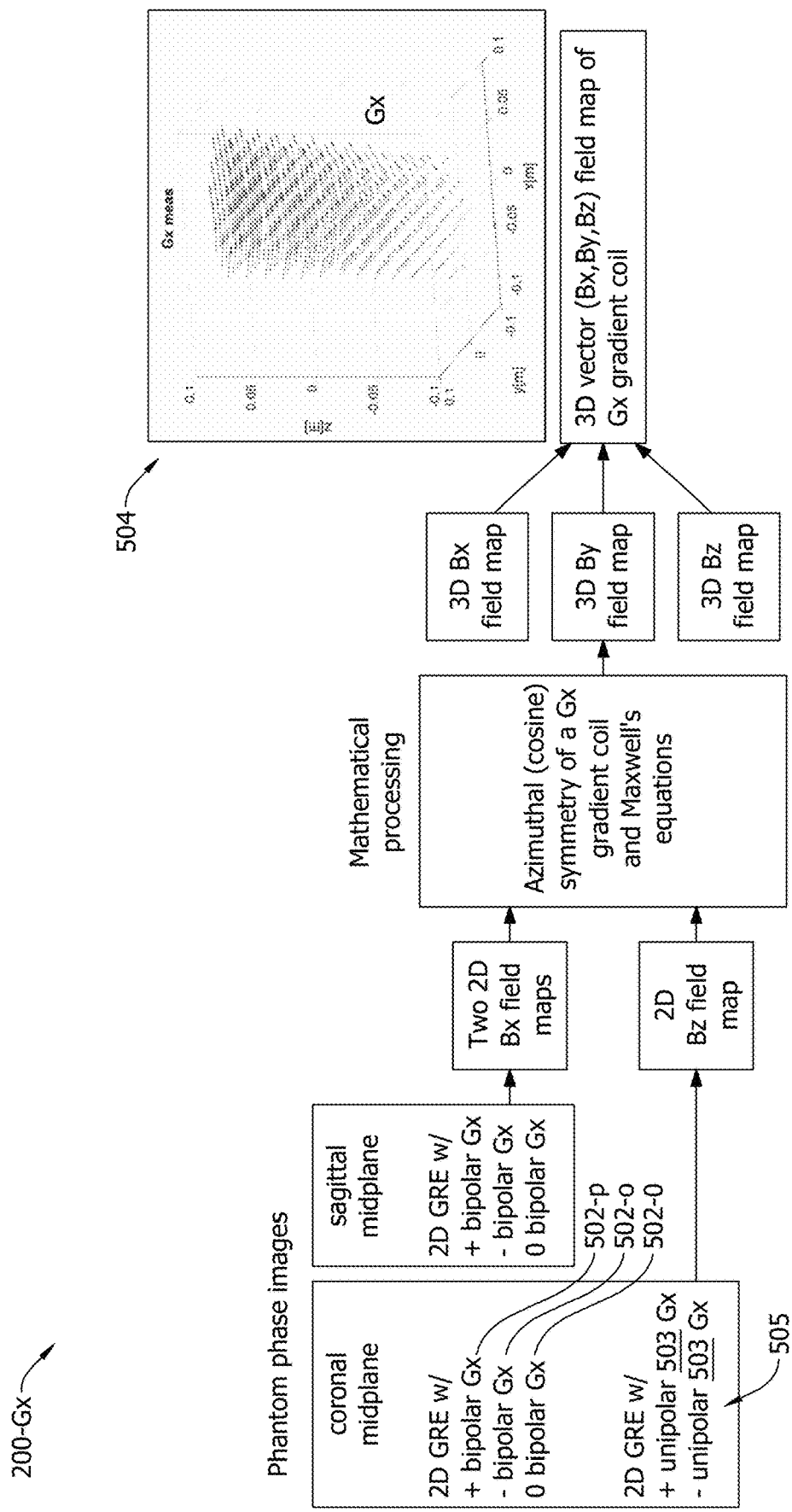
FIG. 5A is a flow chart of measuring concomitant fields of the $G_x$ gradient coil.
Figure 5B:
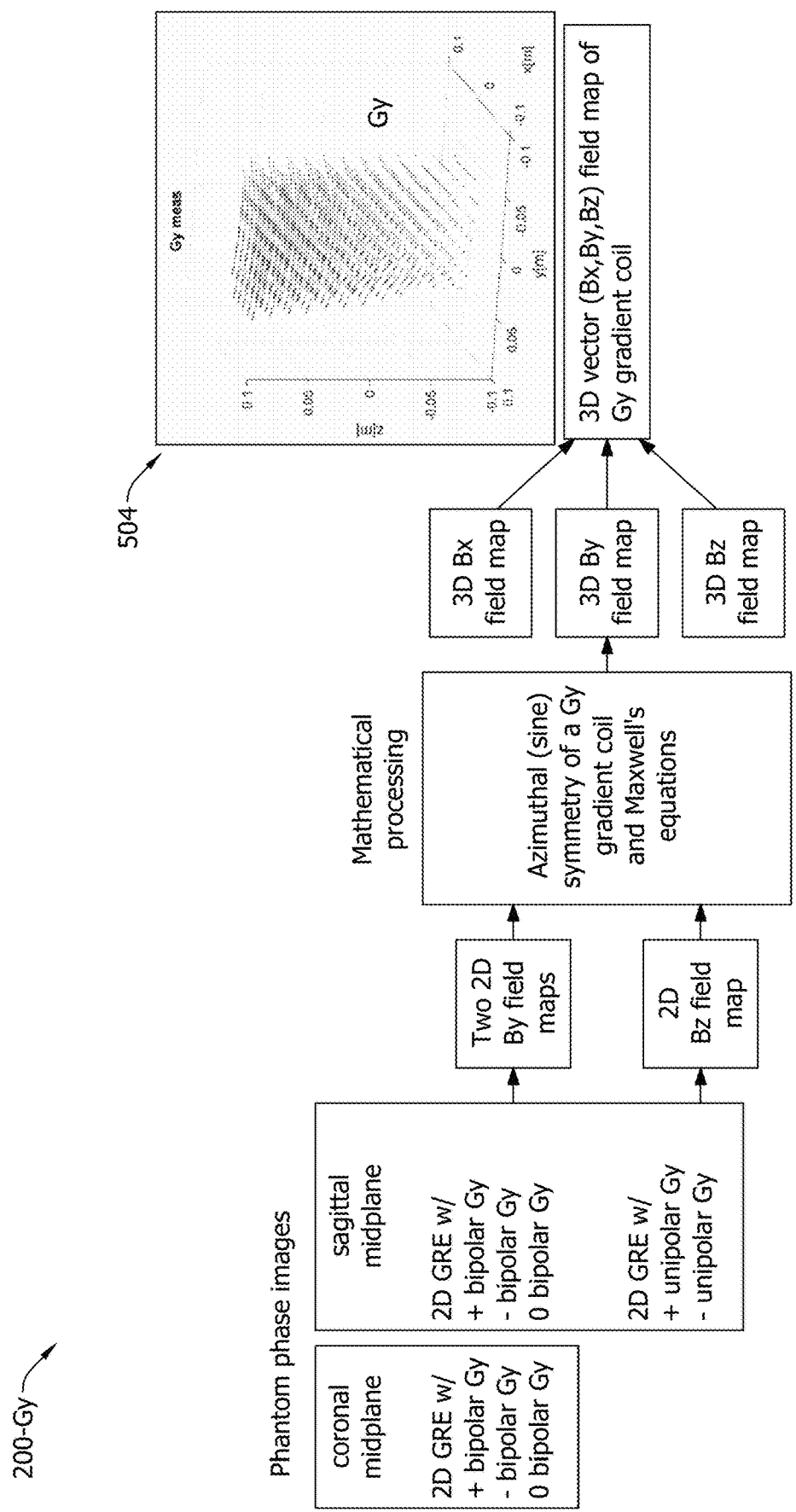
FIG. 5B is a flow chart of measuring concomitant fields of the $G_y$ gradient coil.
Figure 5C:
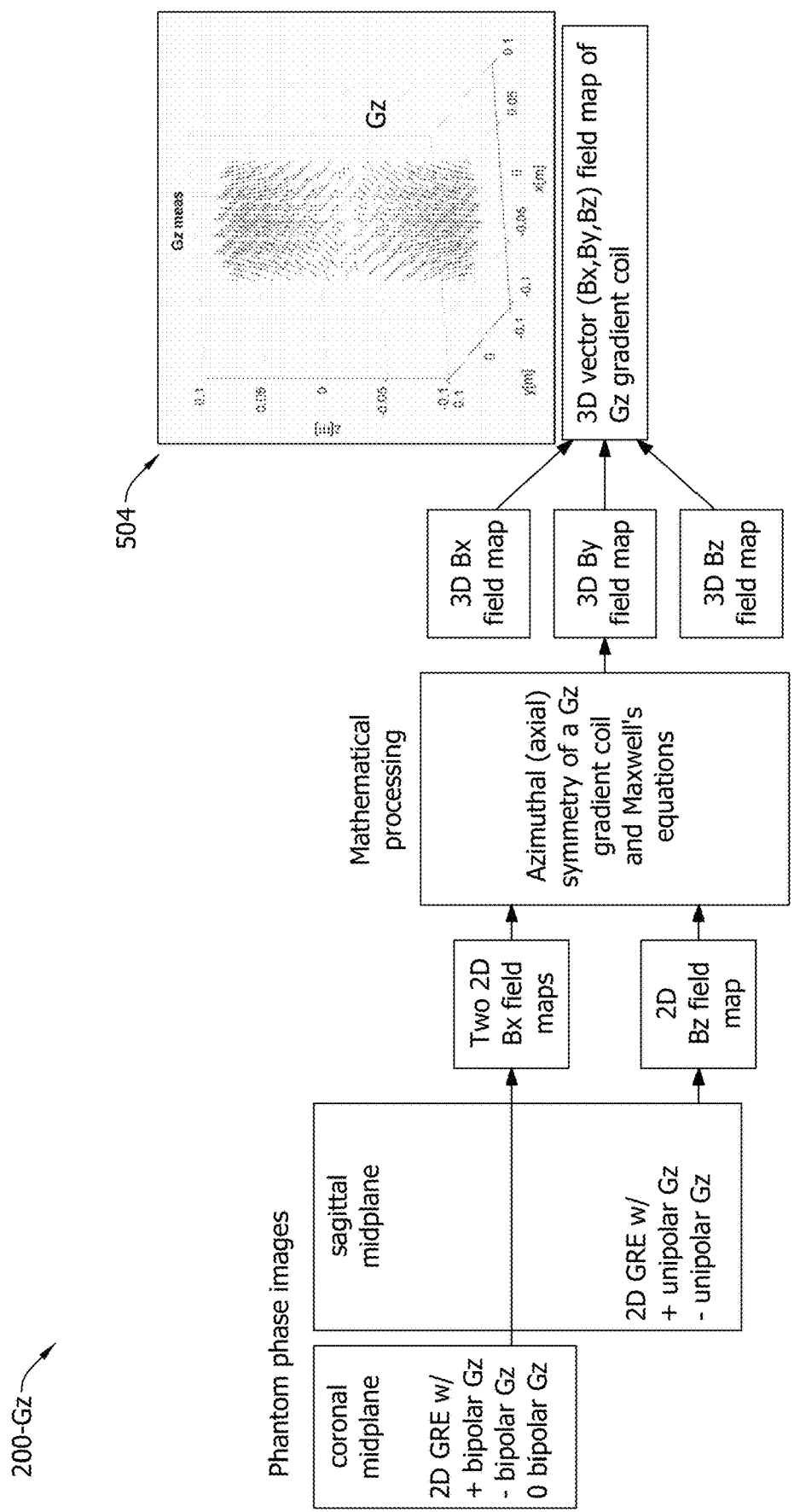
FIG. 5C is a flow chart of measuring concomitant fields of the $G_z$ gradient coil.

FIGS. 5A-5C are schematic diagrams of an example method of generating the volumetric vector field maps of $G_x$, $G_y$, and $G_z$ gradient coils. FIG. 5A shows an example method to measure volumetric vector field maps of the $G_x$ gradient coil. In the example embodiment, to generate a volumetric vector field map of the $G_x$ gradient coil, coronal midplane and sagittal midplane images are acquired.

In the example embodiment, coronal midplane images include a first set and a second set. The first set of coronal midplane images are acquired according to the scheme shown in FIG. 3, where a coronal midplane image with a positive bipolar gradient pulse 502-p, a coronal midplane image with a negative bipolar gradient pulse 502-n, and a coronal midplane image without a bipolar gradient pulse 502-0 are acquired. The first set of images may be referred to as bipolar images. Bipolar gradient pulse 302 is applied along the $G_x$ direction. Field maps at the coronal midplane is generated based on images 502-p, 502-n, and 502-0. The combination of the three phase images cancels susceptibility and eddy current effects, leaving only concomitant phases.

In the example embodiment, the second set of the coronal midplane images include a coronal midplane image with a positive unipolar gradient applied and a coronal midplane image with a negative unipolar gradient applied, both along $G_x$. The second set of images may be referred to as unipolar images. A unipolar gradient pulse includes a gradient field having one polarity, either positive or negative. The unipolar images are used to generate $B_z$ field map, where the transverse fields from the two unipolar acquisitions have much weaker effects on phases than Bz and cancel out one another, leaving the $B_z$ field, which is in the z direction. Unipolar gradient pulses may be referred to as z field measurement gradient pulse 503. The measurement pulse sequence used to measure the z field or z-dependent concomitant field may be referred to as a z field measurement pulse sequence 505. In measuring $G_x$ field maps, the bipolar gradient pulses and unipolar gradient pulses are applied to the $G_x$ gradient coil. In the sagittal midplane images, a positive bipolar image, a negative bipolar image, and a no-bipolar image are acquired at a sagittal midplane. The bipolar images at the coronal midplane and sagittal midplane are used to generate transverse field maps along the coronal midplane and sagittal midplane. According to Eqns. (15), (16), (17), and (18) above, individual components $B_x$ and $B_y$ at any azimuthal angle may be generated based on the transverse field maps along the coronal and sagittal midplanes. Together with the $B_z$ field map, a vector ($B_x$, $B_y$, $B_z$) field map 504 of the concomitant field for the $G_x$ gradient coil is generated, where the map is a 3D or volumetric map with each position (x, y, z) represented with a vector ($B_x$, $B_y$, $B_z$) of magnetic field for the position.

FIG. 5B shows an example method 200-$G_y$ of measuring vector field map of the $G_y$ gradient coil. Compared to method 200-$G_x$ shown in FIG. 5A, unipolar images are acquired in the sagittal midplane to measure the $B_z$ field because in a coronal midplane (y=0), $B_z$ is zero. The bipolar and unipolar gradient pulses are applied to the $G_y$ gradient coil.

FIG. 5C shows an example method 200-$G_z$ of measuring vector field map of the $G_z$ gradient coil. Different from method 200-$G_x$ and 200-$G_y$ shown in FIGS. 5A and 5B, only one set of bipolar midplane images are acquired. The bipolar midplane may be a coronal midplane or a sagittal midplane. Any midplane may be used to measure a transverse field map of the $G_z$ gradient coil for an axi-symmetric $G_z$ coil. A transverse field map with transverse components at positions (x, y) in a plane containing the z-axis other than the acquired midplane may be generated by duplicating the values for the same z and ρ positions. The unipolar images may be acquired in the sagittal or coronal midplane.

Figure 6A:
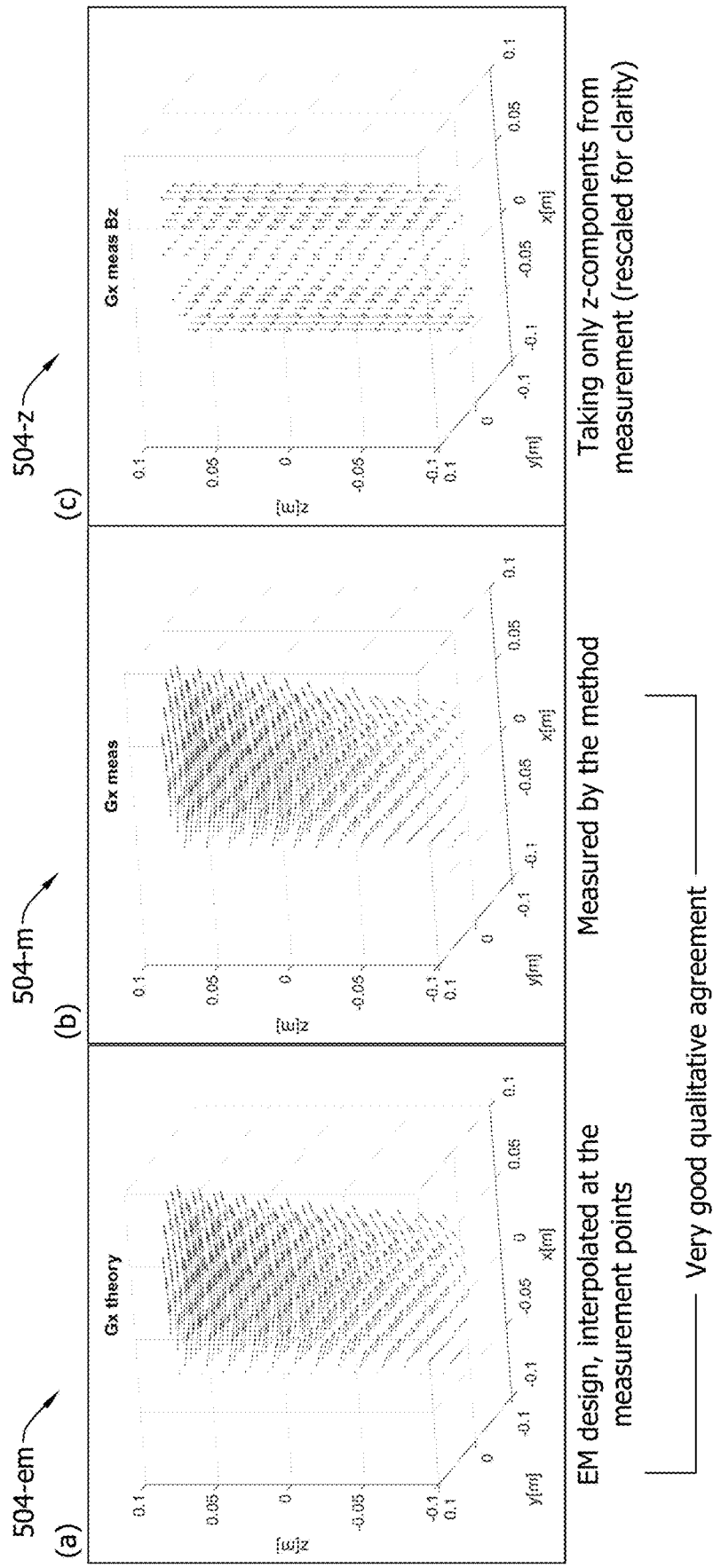
FIG. 6A shows vector field maps of a $G_x$ gradient coil.
Figure 6B:
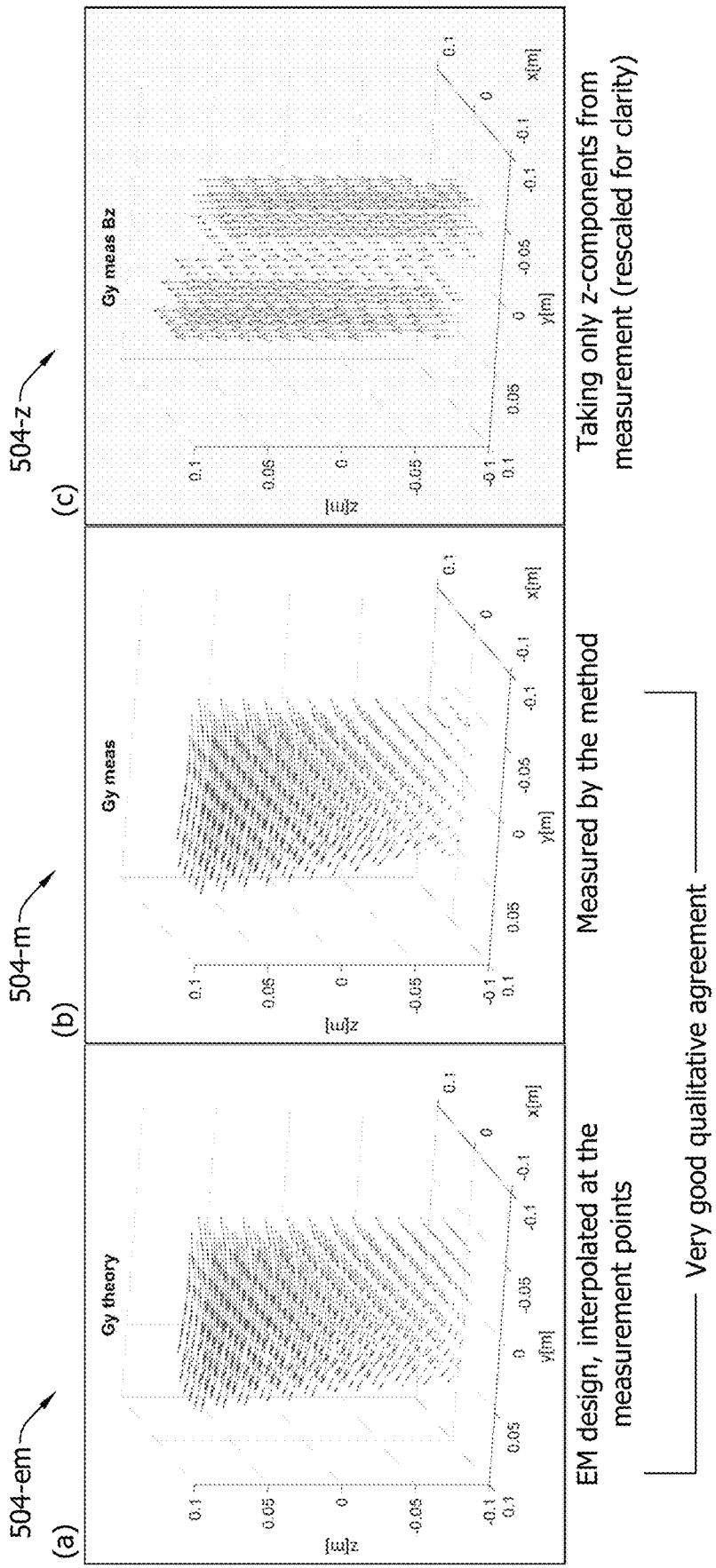
FIG. 6B shows vector field maps of a $G_y$ gradient coil.
Figure 6C:
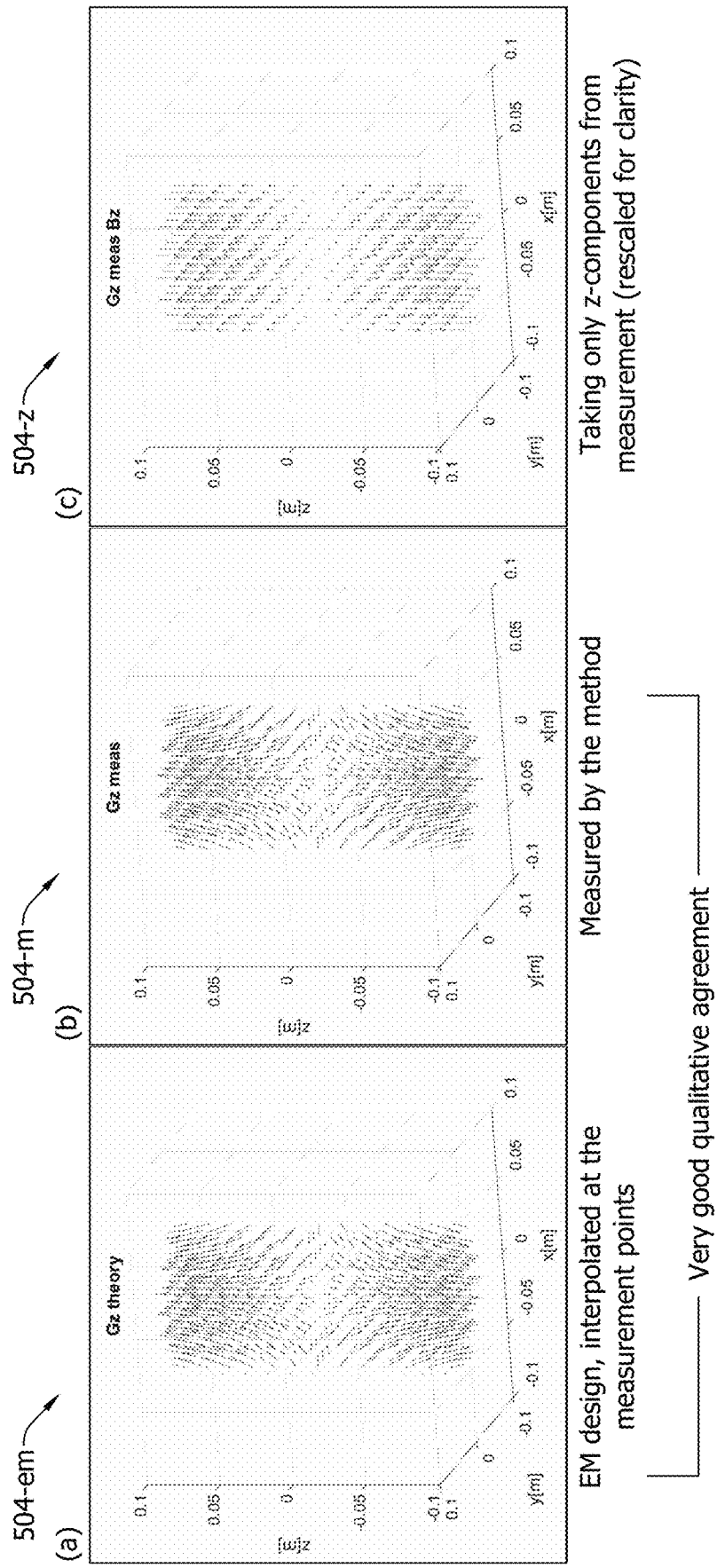
FIG. 6C shows vector field maps of a $G_z$ gradient coil.

FIGS. 6A-6C provide comparisons of the field maps 504-$m$ generated by the systems and methods described herein with field maps 504-$e$ generated using EM design specification of the scanner, and field maps 504-$z$ with only the z components. As shown, the field maps 504-$m$ generated with systems and methods described herein agree with the field maps 504-$e$ based on the EM design.

Figure 7:
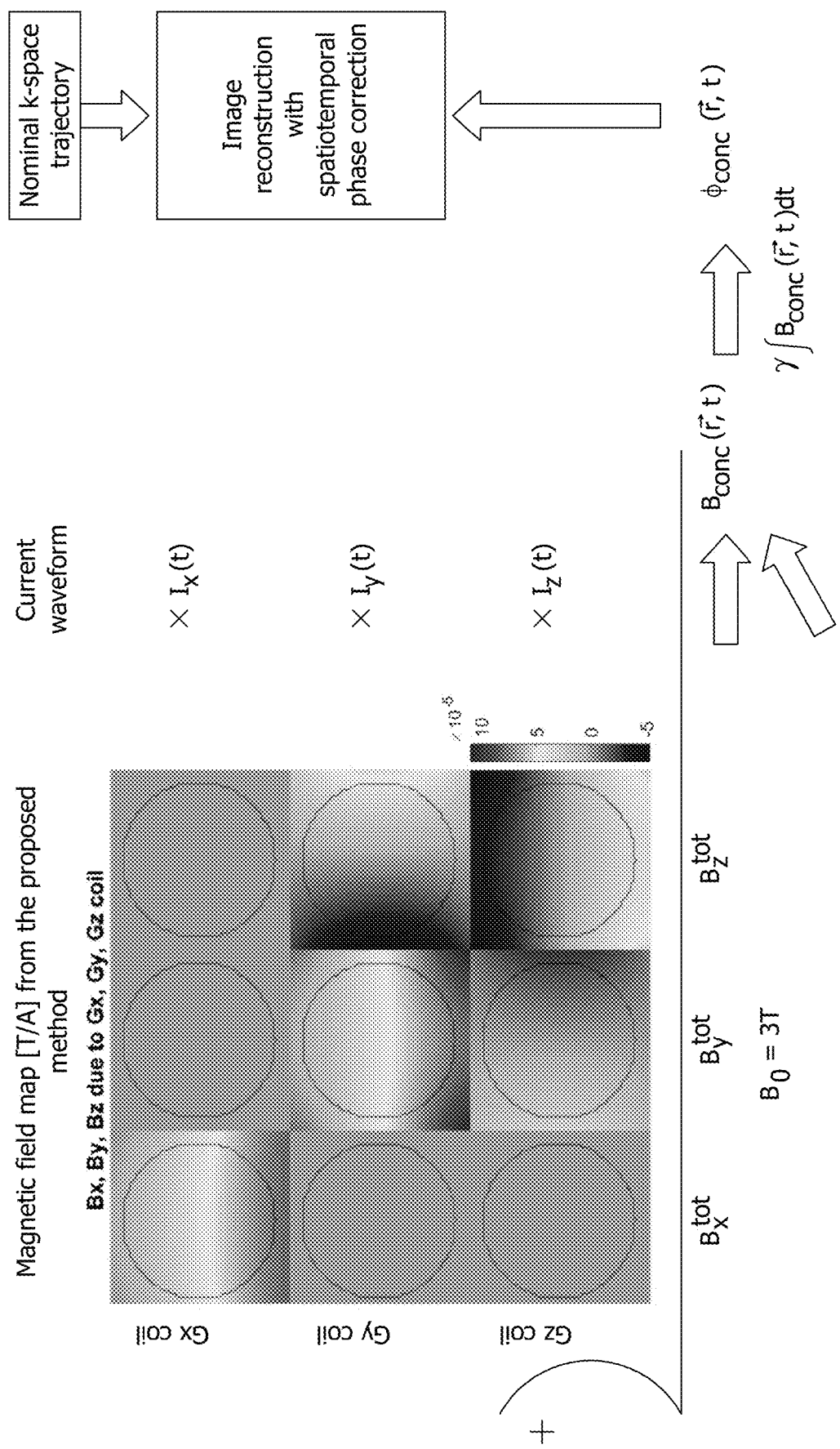
FIG. 7 is a flow chart of an example method of correcting effects of concomitant fields.

FIG. 7 is a schematic diagram of a method of correcting effects from concomitant field using the volumetric vector maps generated using systems and methods described herein. In the example embodiment, normalized volumetric vector maps of the $G_x$, $G_y$, $G_z$ coils are generated, which include the volumetric vector maps for $G_x$, $G_y$, and $G_z$ gradient coils. The normalized volumetric vector maps are normalized maps as per unit of current applied to the coil. For each spatial position (x, y, z), the maps include maps for $G_x$, $G_y$, or $G_z$ coils, where each point in the maps is represented as a vector having $B_x$, $B_y$, and $B_z$ components. The normalized volumetric vector maps are used to generate field maps of any gradient pulse used in the scanning by multiplying the current waveform $I_x(t)$, $I_y(t)$, or $I_z(t)$ to the $G_x$, $G_y$, or $G_z$ map, respectively. As a result, the field $B_{conc}(\vec{r}, t)$ at each spatial location at each time point is generated. The phase experienced at each spatial location and time $\phi_{conc}(\vec{r}, t)$ is generated based on the field, where frequency is proportional to the field and phase is an integral of the frequency over the period of time [0, t]. The concomitant phase image $\phi_{conc}(\vec{r}, t)$ is used in image reconstruction to correct spatiotemporal phase errors caused by concomitant fields. For example, $\phi_{conc}(\vec{r}, t)$ indicates deviations from nominal k-space trajectory, which is the k-space trajectory without phase errors from concomitant field, and is used to locate the actual k-space trajectory. The MR signals or k-space data are processed with the actual k-space trajectory to produce an image of increased accuracy.

Methods described herein may be implemented on any suitable computing device 800 and software implemented therein. Methods described above may be performed on workstation 12 or a separate computing device in wired or wireless communication with workstation 12. A separate computing device may receive data from workstation 12 via a portable storage medium such as a flash drive. Methods described herein may be performed on separate computing devices. Methods or part of methods described herein may be performed on a server computing device.

Figure 8:
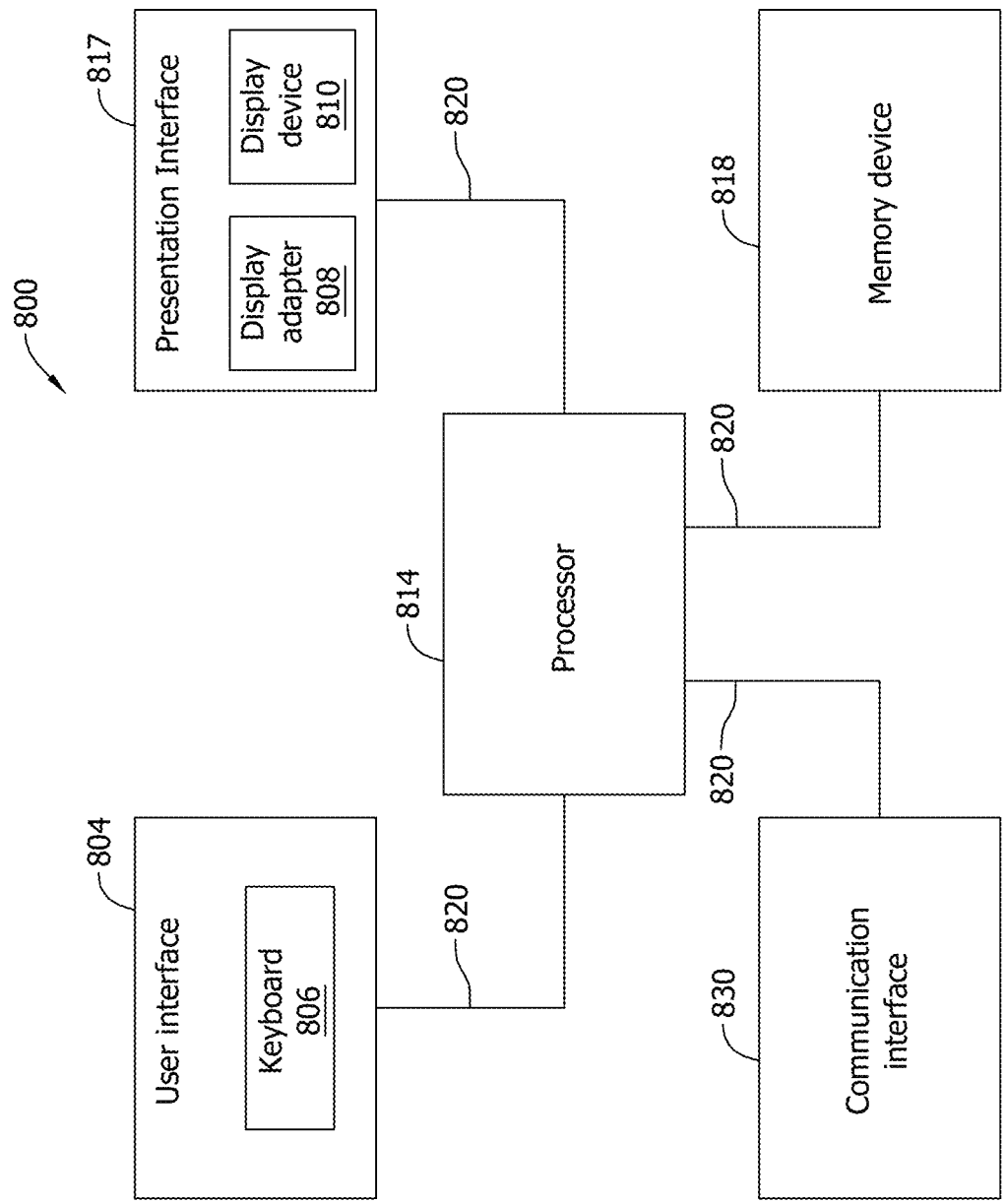
FIG. 8 is a block diagram of an example computing device.

FIG. 8 is a block diagram of an example computing device 800. In the example embodiment, computing device 800 includes a user interface 804 that receives at least one input from a user. User interface 804 may include a keyboard 806 that enables the user to input pertinent information. User interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the example embodiment, computing device 800 includes a presentation interface 817 that presents information, such as input events and/or validation results, to the user. Presentation interface 817 may also include a display adapter 808 that is coupled to at least one display device 810. More specifically, in the example embodiment, display device 810 may be a visual display device, such as a cathode ray tube (CRT), a liquid crystal display (LCD), a light-emitting diode (LED) display, and/or an "electronic ink" display. Alternatively, presentation interface 817 may include an audio output device (e.g., an audio adapter and/or a speaker) and/or a printer.

Computing device 800 also includes a processor 814 and a memory device 818. Processor 814 is coupled to user interface 804, presentation interface 817, and memory device 818 via a system bus 820. In the example embodiment, processor 814 communicates with the user, such as by prompting the user via presentation interface 817 and/or by receiving user inputs via user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are example only, and thus are not intended to limit in any way the definition and/or meaning of the term "processor."

In the example embodiment, memory device 818 includes one or more devices that enable information, such as executable instructions and/or other data, to be stored and retrieved. Moreover, memory device 818 includes one or more computer readable media, such as, without limitation, dynamic random access memory (DRAM), static random access memory (SRAM), a solid state disk, and/or a hard disk. In the example embodiment, memory device 818 stores, without limitation, application source code, application object code, configuration data, additional input events, application states, assertion statements, validation results, and/or any other type of data. Computing device 800, in the example embodiment, may also include a communication interface 830 that is coupled to processor 814 via system bus 820. Moreover, communication interface 830 is communicatively coupled to data acquisition devices.

In the example embodiment, processor 814 may be programmed by encoding an operation using one or more executable instructions and providing the executable instructions in memory device 818. In the example embodiment, processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Figure 9:
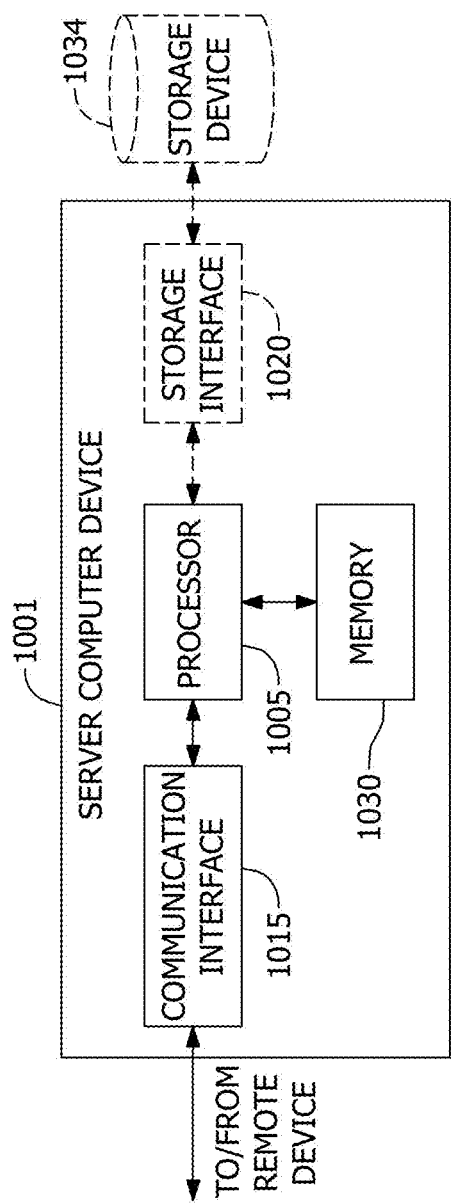
FIG. 9 is a block diagram of an example server computing device.

FIG. 9 illustrates an example configuration of a server computer device 1001. Server computer device 1001 also includes a processor 1005 for executing instructions. Instructions may be stored in a memory area 1030, for example. Processor 1005 may include one or more processing units (e.g., in a multi-core configuration).

Processor 1005 is operatively coupled to a communication interface 1015 such that server computer device 1001 is capable of communicating with a remote device or another server computer device 1001. For example, communication interface 1015 may receive data from workstation 12, via the Internet.

Processor 1005 may also be operatively coupled to a storage device 1034. Storage device 1034 is any computer-operated hardware suitable for storing and/or retrieving data. In some embodiments, storage device 1034 is integrated in server computer device 1001. For example, server computer device 1001 may include one or more hard disk drives as storage device 1034. In other embodiments, storage device 1034 is external to server computer device 1001 and may be accessed by a plurality of server computer devices 1001. For example, storage device 1034 may include multiple storage units such as hard disks and/or solid state disks in a redundant array of independent disks (RAID) configuration. storage device 1034 may include a storage area network (SAN) and/or a network attached storage (NAS) system.

In some embodiments, processor 1005 is operatively coupled to storage device 1034 via a storage interface 1020. Storage interface 1020 is any component capable of providing processor 1005 with access to storage device 1034. Storage interface 1020 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1005 with access to storage device 1034.

At least one technical effect of the systems and methods described herein includes (a) providing measurement of concomitant fields without assumption of gradient linearity; (b) isolating concomitant fields from other perturbation to the magnetic field; (c) a measurement pulse sequence for measuring concomitant fields; (d) generating 3D vector field maps of a gradient coil; and (e) providing correction field maps of an arbitrary imaging gradient pulse sequence.

Example embodiments of systems and methods of measuring and correcting concomitant field effects are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for measuring concomitant fields in a magnetic resonance (MR) system, comprising:
applying a measurement pulse sequence in a plurality of acquisitions with a subject positioned in an MR system, applying the measurement pulse sequence further comprises:
applying a first bipolar gradient pulse in a first acquisition;
applying a second bipolar gradient pulse in reverse polarities from the first bipolar gradient pulse in a second acquisition; and
applying the measurement pulse sequence without a bipolar gradient pulse in a third acquisition;
acquiring MR signals emitted from the subject;
generating phase images based on the MR signals;
generating volumetric vector field maps based on the phase images, wherein the volumetric vector field maps include concomitant field at each spatial location in a three-dimensional (3D) volume, the concomitant field represented as a vector; and
outputting the volumetric vector field maps.

2. The method of claim 1, wherein:
generating phase images further comprises:
generating a first phase image corresponding to the first acquisition based on the MR signals acquired during the first acquisition;
generating a second phase image corresponding to the second acquisition based on the MR signals acquired during the second acquisition; and
generating a third phase image corresponding to the third acquisition based on the MR signals acquired during the third acquisition; and
generating volumetric vector field maps further comprises:
isolating the concomitant fields from other perturbation fields of the MR system by combining the first phase image, the second phase image, and the third phase image.

3. The method of claim 2, wherein isolating the concomitant fields further comprises: adding the second phase image to the first phase image; and
subtracting the third phase image from a half of a sum of the first phase image and the second phase image to derive a combination phase image,
wherein the concomitant fields are isolated from other perturbation fields in the combination phase image.

4. A method for measuring concomitant fields in a magnetic resonance (MR) system, comprising:
applying a measurement pulse sequence in a plurality of acquisitions with a subject positioned in an MR system, wherein applying a measurement pulse sequence further comprises varying the measurement pulse sequence in the plurality of acquisitions;
acquiring MR signals emitted from the subject;
generating phase images based on the MR signals;
isolating concomitant fields from other perturbation fields of the MR system based on the phase images;
generating volumetric vector field maps based on the phase images, wherein the volumetric vector field maps include concomitant field at each spatial location in a three-dimensional (3D) volume, and the concomitant field is represented as a vector; and
outputting the volumetric vector field maps.

5. The method of claim 4, wherein:
generating phase images further comprises:
generating the phase images for each of the plurality of acquisitions; and
isolating concomitant fields further comprises isolating the concomitant fields by combining the phase images of the plurality of acquisitions.

6. The method of claim 4, wherein applying a measurement pulse sequence further comprises:
measuring transverse concomitant fields by:
applying the measurement pulse sequence along a coronal midplane; and
applying the measurement pulse sequence along a sagittal midplane.

7. The method of claim 6, wherein generating volumetric vector field maps further comprises:
generating x components of the volumetric vector field maps and y components of the volumetric vector field maps based on a first phase image corresponding to the coronal midplane and a second phase image corresponding to the sagittal midplane.

8. The method of claim 7, wherein generating x components of the volumetric vector field maps and y components of the volumetric vector field maps further comprises:
generating an x component at a spatial location by applying a first function of a radial distance and an azimuthal angle of the spatial location to the first phase image and the second phase image; and
generating a y component at the spatial location by applying a second function of the radial distance and the azimuthal angle to the first phase image and the second phase image.

9. The method of claim 4, wherein generating volumetric vector field maps further comprises:
normalizing the volumetric vector field maps with a current carried by a gradient coil in applying the measurement pulse sequence.

10. The method of claim 4, wherein the method further comprises:
generating correction field maps by multiplying the volumetric vector field maps with a current of an imaging pulse sequence, wherein the current is represented as a function of time, and the correction field maps are spatiotemporal functions.

11. The method of claim 4, wherein applying a measurement pulse sequence further comprises:
applying the measurement pulse sequence in a plurality of acquisitions by:
applying a first bipolar gradient pulse in a first acquisition;
applying a second bipolar gradient pulse in reverse polarities from the first bipolar gradient pulse in a second acquisition; and
applying the measurement pulse sequence without a bipolar gradient pulse in a third acquisition.

12. The method of claim 11, wherein:
generating phase images further comprises:
generating a first phase image corresponding to the first acquisition based on the MR signals acquired during the first acquisition;
generating a second phase image corresponding to the second acquisition based on the MR signals acquired during the second acquisition; and
generating a third phase image corresponding to the third acquisition based on the MR signals acquired during the third acquisition; and isolating concomitant fields further comprises:
isolating the concomitant fields by combining the first phase image, the second phase image, and the third phase image.

13. The method of claim 12, wherein isolating concomitant fields further comprises:
adding the second phase image to the first phase image; and
subtracting the third phase image from a half of a sum of the first phase image and the second phase image to derive a combination phase image,
wherein the concomitant fields are isolated from other perturbation fields in the combination phase image.

14. The method of claim 4, wherein the measurement pulse sequence includes measurement gradient pulses, and for a gradient coil of a gradient coil assembly of the MR system, the method further comprises:
applying the measurement gradient pulses on the gradient coil; and
generating volumetric vector field maps of the gradient coil.

15. The method of claim 14, wherein the gradient coil is an x gradient coil or a y gradient coil, and applying a measurement pulse sequence further comprises:
applying the measurement pulse sequence along a first slice; and
applying the measurement pulse sequence along a second slice rotated 90° from the first slice along a z axis of the MR system.

16. The method of claim 14, wherein the gradient coil is a z gradient coil, and applying a measurement pulse sequence further comprises:
applying the measurement pulse sequence along a coronal midplane or a sagittal midplane.

17. The method of claim 4, wherein:
applying a measurement pulse sequence further comprises:
measuring a z field by:
applying a first unipolar gradient pulse in a first acquisition; and
applying a second unipolar gradient pulse having reverse polarities from the first unipolar gradient pulse in a second acquisition; and
generating volumetric vector field maps further comprises:
generating z components of the volumetric vector field maps based on the MR signals acquired during measuring the z field.

18. A method for measuring concomitant fields in a magnetic resonance (MR) system, comprising:
measuring transverse concomitant fields by applying a measurement pulse sequence in a plurality of acquisitions, applying a measurement pulse sequence further comprising varying the measurement pulse sequence in the plurality of acquisitions; and
measuring a z field by applying the measurement pulse sequence including a z field measurement pulse sequence.

19. The method of claim 18, wherein the measurement pulse sequence includes measurement gradient pulses, and measuring transverse concomitant fields further comprises:
measuring the transverse concomitant fields of a transverse gradient coil of a gradient coil assembly of the MR system by:
applying the measurement gradient pulses on the transverse gradient coil along a first slice; and applying the measurement gradient pulses on the transverse gradient coil along a second slice rotated 90° from the first slice along a z axis of the MR system.

20. The method of claim 18, wherein the measurement pulse sequence includes measurement gradient pulses, and measuring transverse concomitant fields further comprises:
  measuring concomitant fields of a z gradient coil of a gradient coil assembly of the MR system by:
    applying the measurement gradient pulses on the z gradient coil along a slice.

\* \* \* \* \*